United States Patent [19]

Tyers et al.

[11] Patent Number: 5,578,628

[45] Date of Patent: *Nov. 26, 1996

[54] MEDICAMENTS FOR THE TREATMENT OF NAUSEA AND VOMITING

[75] Inventors: Michael B. Tyers, Welwyn; Ian H. Coates, Hertford; David C. Humber, Ealing; George B. Ewan, Chalfont St. Peter; James A. Bell, Melbourn, all of England

[73] Assignee: Glaxo Group Limited, England

[*] Notice: The portion of the term of this patent subsequent to Feb. 16, 2005, has been disclaimed.

[21] Appl. No.: 501,974

[22] Filed: Mar. 30, 1990

Related U.S. Application Data

[60] Continuation of Ser. No. 315,314, Feb. 24, 1989, abandoned, which is a division of Ser. No. 177,042, Apr. 4, 1988, Pat. No. 4,929,632, which is a division of Ser. No. 877,805, Jun. 24, 1986, Pat. No. 4,753,789.

[30] Foreign Application Priority Data

Jun. 25, 1985 [GB] United Kingdom ............... 8516083

[51] Int. Cl.[6] .................................................. A61K 31/415
[52] U.S. Cl. .................................................. 514/397
[58] Field of Search ........................... 514/397; 548/336, 548/439

[56] References Cited

U.S. PATENT DOCUMENTS

| | | | |
|---|---|---|---|
| 4,721,720 | 1/1988 | Wootton et al. | 514/304 |
| 4,725,615 | 2/1988 | Coates | 514/397 |
| 4,749,718 | 6/1988 | Coates | 514/397 |
| 4,753,789 | 6/1988 | Tyers | 514/397 |
| 4,783,478 | 11/1988 | Wootton et al. | 514/397 |
| 4,929,632 | 5/1990 | Tyers | 514/397 |

FOREIGN PATENT DOCUMENTS

| | | |
|---|---|---|
| 8506642 | 3/1985 | United Kingdom . |
| 8509039 | 4/1985 | United Kingdom . |
| 8531614 | 12/1985 | United Kingdom . |

*Primary Examiner*—Raymond Henley, III
*Attorney, Agent, or Firm*—Bacon & Thomas

[57] ABSTRACT

The invention relates to the use of compounds of the general formula (I)

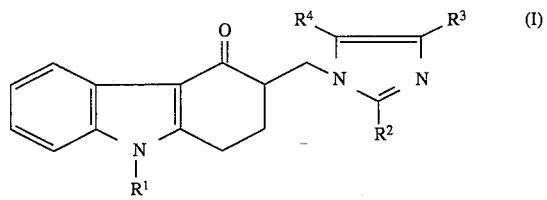

wherein $R^1$ represents a hydrogen atom or a $C_{1-10}$ alkyl, $C_{3-7}$ cycloalkyl, $C_{-7}$ cycloalkyl-$(C_{1-4})$ alkyl, $C_{3-6}$ alkenyl, $C_{3-10}$ alkynyl, phenyl or phenyl-$C_{1-3}$ alkyl group; and one of the groups represented by $R^2$, $R^3$ and $R^4$ is a hydrogen atom or a $C_{1-6}$ alkyl, $C_{3-7}$cycloalkynyl, $C_{2-6}$ alkenyl or phenyl-$C_{1-3}$ alkyl group and each of the other two groups, which may be the same or different, represents a hydrogen atom or a $C_{1-6}$ alkyl group; and physiologically acceptable salts and solvates thereof, for the relief of nausea and vomiting.

2 Claims, No Drawings

MEDICAMENTS FOR THE TREATMENT OF NAUSEA AND VOMITING

This application is a CONTINUATION of application Ser. No. 07/315,314, filed Feb. 24, 1989, now abandoned, which is a DIVISION of application. Ser. No. 07/177,042, filed Apr. 4, 1988, now U.S. Pat. No. 4,929,632, which is a DIVISION of application Ser. No. 06/877,805, filed Jun. 24, 1986, now U.S. Pat. No. 4,753,789.

This invention relates to a new medical use for a group of heterocyclic compounds and pharmaceutical compositions containing them. In particular it relates to certain tetrahydocarbazolone derivatives which may be used to promote gastric emptying and as anti-emetic agents.

A particularly important application for anti-emetic agents is in the prevention and treatment of nausea and vomiting associated with cancer chemotherapy. Emesis is a well-known and frequent side-effect of cancer chemotherapeutic agents, such as cisplatin. It causes serious problems in cancer chemotherapy, and in some patients emesis is so severe that therapy must be discontinued. Anti-emetic agents are therefore often administered in order to alleviate this side-effect of the cancer chemotherapeutic agent. The anti-emetic agents employed are usually benzamide derivatives, such as metoclopramide, which have dopamine antagonist activity.

Metoclopramide is also a gastric mobility stimulant, i.e. it promotes gastric emptying. The promotion of gastric emptying is important in the treatment of gastro-intesinal disorders related to gastric stasis; and in radiological examinations.

In view of their dopamine antagonist activity benzamide derivatives such as metoclopramide themselves exhibit serious and undesirable side-effects, such as extra-pyramidal effects, i.e. tardive dyskinesia, acute distonia, akathisia and tremor. There is thus a need for a safe and effective anti-emetic agent and gastric mobility stimulant.

In our British patent application No. 2153821A and our European patent application No. 86300423 we disclose 3-imidazolylmehyltetrahydrocazbazolones which may be represented by the general formula (I)

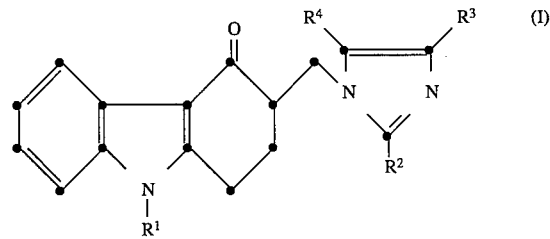

wherein
$R^1$ represents a hydrogen atom or a $C_{1-10}$ alkyl, $C_{3-7}$ cycloalkyl, $C_{3-7}$cycloalkyl-$(C_{1-4})$alkyl, $C_{3-6}$ alkenyl, $C_{3-10}$alkynyl, phenyl or phenyl-$C_{1-3}$alkyl group, and one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-$C_{1-3}$alkyl group and each of the other two groups, which may be the same or different, represents a hydrogen atom or a $C_{1-6}$ alkyl group;
and physiologically acceptable salts and solvates, e.g. hydrates, thereof.

Suitable physiologically acceptable salts of the carbazolones of general formula (I) include acid addition salts formed with organic or inorganic acids for example, hydrochlorides, hydrobromides, sulphates, phosphates, citrates, fumarates and maleates. The solvates may, for example, be hydrates.

The aforementioned specifications also disclose physiologically acceptable equivalents of the compounds of formula (I), i.e. physiologically acceptable compounds which are converted in vivo into the parent compound of formula (I).

The compounds of formula (I) are described in the aforementioned specifications as potent and selective antagonists of 5-hydroxytryptamine (5-HT) at 'neuronal' 5-HT receptors of the type located on terminals of primary afferent nerves, and which are also believed to be present in the central nervous system. The compounds are described as being of use in the treatment of a human or animal subject suffering from a condition caused by a disturbance of neuronal 5HT function, for example in the treatment of a human subject suffering from migraine pain or a psychotic disorder such as schizophrenia. It is also stated that the compounds may be useful in the treatment of conditions such as anxiety, obesity and mania.

We have now surprisingly found that compounds of formula (I) promote gastric emptying and also that they are anti-emetic.

Accordingly, the invention provides a method of treatment for the relief of nausea and vomiting, and/or the promotion of gastric emptying e.g. for the relief of gastro-intestinal disorders associated with gastric stasis, which comprises administering to a human or animal subject an effective amount of a compound of formula (I), or a physiologically acceptable salt or solvate thereof.

Tests in animals have shown that compounds of formula (I) enhance gastric emptying. The compounds are therefore of use in the treatment and/or prevention of conditions which may be relieved by the promotion of gastric emptying e.g. gastric stasis which may occur, for example, post-operatively, and symptoms of gastro-intestinal dysfunction such as occur with dyspepsia, peptic ulcer, reflux oesophagitis and flatulence. The compounds may also be used to promote gastric emptying in diagnostic radiological procedures, such as radiological examinations.

Tests in animals have also shown that compounds of formula (I) inhibit emesis. The compounds are therefore also of use as anti-emetic agents, i.e. in the prevention and treatment of nausea and vomiting. The compounds are especially valuable for the prevention of emesis induced by cancer chemotherapeutic agents such as cisplatin. Particular mention may also be made of the treatment of radiation-induced emesis. Thus, the compounds of formula (I) may be used in the prevention of emesis induced by radiation therapy, e.g. irradiation of the thorax or abdomen, such as in the treatment of cancer; or in the treatment of radiation sickness.

The compounds of formula (I) do not possess dopamine antagonist activity and thus will not produce the undesirable side effects found with known anti-emetic agents such as metoclopramide.

It will be appreciated that the compounds of formula (I) may be used prophylactically and references in this specification to treatment include prophylactic treatment as well as the alleviation of acute symptoms.

A preferred class of compounds for use according to the invention is that represented by the formula (Ia):

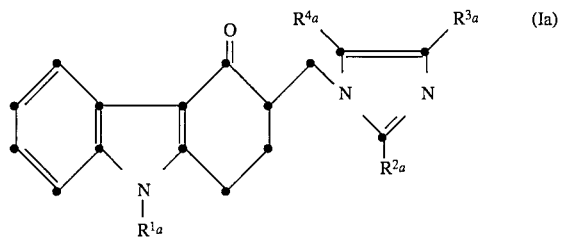

(wherein $R^{1a}$ represents a hydrogen atom or a methyl, ethyl, propyl, prop-2-yl, prop-2-enyl or cyclopentyl group; $R^{3a}$ represents a hydrogen atom; and either $R^{2a}$ represents a methyl, ethyl, propyl or prop-2-yl group and $R^{4a}$ represents a hydrogen atom or $R^{2a}$ represents a hydrogen atom and $R^{4a}$ represents a methyl or ethyl group) and physiologically acceptable sales and solvates (e.g. hydrates) thereof.

Preferred compounds for use according to the present invention are:
1,2,3,9-tetrahydro-3[(2-methyl-1H-imidazol-1-yl)methyl]-9-(prop-2-enyl)-4H-carbazol-4-one;
9-cyclopentyl-1,2,3,9-tetrahydro-3-[(2-methyl-1H-imidazol-1-yl)methyl]-4H-carbazol-4-one; and
1,2,3,9-tetrahydro-3-[(2-methyl-1H-imidazol-1 -yl)methyl]-9-(prop-2-yl)-4H-carbazol-4-one and their physiologically acceptable salts and solvates.

A particularly preferred compound is 1,2,3,9-tetrahydro-9-methyl-3-[(2-methyl-1H-imidazol-1-yl)methyl]-4H-carbazol-4-one, and the physiologically acceptable salts and solvates (e.g. hydrates) thereof. A preferred form of his compound is the hydrochloride dihydrate.

The compounds of formula (Ia) are well absorbed from the gastro-intestinal tract. They do not prolong sleeping time in the pentobarbiton anaesthetised mouse indicating that there is no undesirable interaction with drug metabolising enzymes. Indeed they exhibit no effects on normal behaviour, are non-toxic and exhibit no undesirable effects in mice at doses up to 1 mg/kg intravenously.

Accordingly, the invention also provides a pharmaceutical composition which comprises at least one compound selected from 3-imidazolylmethyltetrahydrocarbazolone derivatives of the general formula (I), their physiologically acceptable salts and solvates, e.g. hydrates, for use in human or veterinary medicine, for the relief of nausea and vomiting and/or the promotion of gastric emptying e.g. for the relief of gastro-intestinal disorders associated with gastric stasis.

In a yet further aspect, the invention provides the use of a compound of formula (I) or a physiologically acceptable salt or solvate thereof, for the manufacture of a medicament for the relief of nausea and vomiting, and/or the promotion of gastric emptying e.g. for the relief of gastro-intestinal disorders associated with gastric stasis.

Pharmaceutical compositions for use in accordance with the present invention may be formulated in conventional manner using one or more physiologically acceptable carriers or excipients.

Thus the compounds of formula (I) and their physiologically acceptable salts and solvates may be formulated for oral, buccal, parenteral or rectal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (I) may be formulated or parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (I) may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds of formula (I) may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds for use according to the present invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of formula (I) and a suitable powder base such as lactose or starch.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

A proposed dose of the compounds of the invention for administration in man (of approximately 70 kg body weight) is 0.05 to 20 mg, preferably 0.1 to 10 mg of the active ingredient per unit dose which could be administered, for example, 1 to 4 times per day. The dose will depend on the route of administration and the body weight of the patient. It will be appreciated that it may be necessary to make routine variations to the dosage depending on the age and weight of the patient as well as the severity of the condition to be treated.

For oral administration a unit dose will preferably contain from 0.5 to 8 mg of the active ingredient. A unit dose for parenteral administration will preferably contain 0.1 to 8 mg of the active ingredient.

Aerosol formulations are preferably arranged so that each metered dose or 'puff' delivered from a pressurised aerosol contains 0.2 mg to 4 mg of a compound of the invention, and each dose administered via capsules and cartridges in an insufflator or an inhaler contains 0.2 to 20 mg of a compound of the invention. The overall daily dose by inhalation will be within the range 0.4 to 80 mg. Administration may be several times daily, for example from 2 to 8 times, giving for example 1, 2 or 3 doses each time.

The compounds of formula (I) may be administered in combination with other therapeutic agents, for example to aid absorption of the therapeutic agent where this is hindered by the patient's condition, such as by gastric stasis associated with migraine. Thus, for example, the compounds may be administered in combination with antimigraine agents such as ergotamine, or antisecretory agents such as ranitidine. They may also be administered in combination with anticancer (e.g. cytostatic) drugs, for example to prevent nausea and vomiting associated with these agents. Cytostatic agents with which compounds of formula (I) may be administered include cyclophosphamide; alkylating agents; and platinum complexes such as cisplatin. Thus, a compound of formula (I) may be presented together with another therapeutic agent as a combined preparation for simultaneous, separate or sequential use, for the relief of nausea and vomiting, or gastrointestinal disorders associated with gastric stasis. Such a combined preparation may be, for example, a twin-pack. A preferred combination comprises a compound of formula (I) with a cytostatic agent, especially cisplatin. In general, the presently available dosage forms of the known therapeutic agents will be suitable for use in such combined preparations. Thus, cisplatin may be provided in vials containing 10, 25 or 50 mg of the active ingredient.

The compounds of general formula (I) may be prepared by the process described in British patent application No. 2153821A. Analogous processes are also described in European patents application No. 86300423.

The efficacy of compounds of formula (I) in the promotion of gastric emptying and their anti-emetic activity have been demonstrated in standard animal models as described below.

(A) GASTRIC EMPTYING

Test compound:
1,2,3,9-tetrahydro-9-methyl-3-[(2-methyl-1H-imidazol-1-yl)methyl]-4H-carbazol-4-one hydrochloride dihydrate The effect of the test compound on gastric emptying was determined in guinea-pigs by following the progress of polystyrene-coated barium sulphate spheres (1 mm diameter) through the gut. The experimental method was based on that described by B. Costall et. al., Eur. J. Pharmacol 91, 197–205, 1983 and B. Cox et. al., Br. J Pharmacol. 70, 104, 1980.

The spheres (approximatley 30 in number) were administered orally in 0.2 ml carboxymethylcellulose with 0.05 ml glycerine. At the same time, the test compound was administered intraperitoneally at doses of 0.001, 0.01 and 0.1 mg/kg. The control animals received saline, administered intraperitoneally, in place of the test compound. Passage of the spheres through the gut was monitored at 30–60 minute intervals over a period of 2 hours by X-ray location. The number of spheres leaving the stomach was recorded and expressed as a percentage of the total.

The results are given in Table 1 below:

TABLE 1

| Effect on test compound on gastric emptying in the guinea pig | | | |
|---|---|---|---|
| Dose of test compound | | Mean % Increase in gastric emptying ($\pm$ s.e.) | |
| (mg/kg, i.p.)* | n | 1 hour | 2 hours |
| 0.001 | 4 | 21 $\pm$ 8.7 | 57 $\pm$ 10.5 |
| 0.01 | 4 | 33 $\pm$ 3.6 | 76.5 $\pm$ 11.2 |
| 0.1 | 4 | 47 $\pm$ 7.6 | 68 $\pm$ 5.0 |
| Saline | 5 | 10 $\pm$ 3.7 | 30 $\pm$ 8.5 |

*Dose expressed as coresponding weight of free base
n = number of animals
s.e. = standard error (B) ANTI-EMESIS Test compound:
1,2,3,9-tetrahydro-9-methyl-3-[(2-methyl-1H-imidazol-1-yl)methyl]-4H-carbazol-4-one hydrochloride dihydrate The effect of the test compound on emesis was demonstrated in ferrets according to the general method described by Florezyk, Schurig and Bradnet (Cancer Treatment Report, 1982 66(1) 187–9) and summarised below. Both the test compound and cisplatin were prepared and administered in normal saline. The dose of test compound was calculated as the free base.

a) Control—Without Test Compound

Emesis was induced in groups of 6 male ferrets weighing between 1.5–2 kg, by intravenous administration of cisplatin at a dose of 10 mg/kg. The onset of emesis occurred between 38 and 75 minutes after injection and over a period of 2 hours the number of vomits/retches (episodes) was in the range 30–62 (average 42$\pm$5 vomits/retches per 2 h). Behavioural changes characteristic of emesis were also noted.

b) With Test Compound

The test compound was administered to groups of 6 male ferrets (1.5–2 kg) by intravenous administration at doses of 0.01, 0.1 and 1 mg/kg, immediately prior to administration of cisplatin as described above. The animals were observed for 3 hours.

The results obtained are given in Table 2 below.

TABLE 2

| Compound | Onset of emesis (minutes) | Intensity of emesis (episodes 2 h) | Duration of emesis (hours) | Other observations |
|---|---|---|---|---|
| Cisplatin (10 mg/kg i.v.) (control) | 38–75 | 42 ± 5 | 2 | Behavioural changes characteristic of emesis (e.g. increased or irregular respiration, backward locomotion, agitation) |
| Cisplatin (10 mg/kg i.v.) + Test Compound 0.01 mg/kg i.v. | 89–109 | 17 ± 2.9 | 1 | Marked reduction in behavioural effects of cisplatin. In second onset of emesis, the animals rested quietly and some slept |
| 0.1 mg/kg i.v. | | | | Emesis and behavioural changes were completely eliminated. After 30–40 minutes the animals rested quietly, and some slept. |
| 1 mg/kg i.v. | | | | |

The effect of the test compound on emesis was also demonstrated following intraperitoneal administration, using a similar procedure to that described above.

Thus cisplatin was administered intraperitoneally to a group of 4 male ferrets at a dose of 9 mg/kg, and the time to onset of emesis and the number of emetic episodes were recorded. In a second group of four male ferrets the test compound was administered at a dose of 1 mg/kg i.p. 30 minutes before and 1 hour after intraperitoneal administration of cisplatin. The results are given in Table 3:

TABLE 3

| Compound | Onset of emesis (minutes) | Mean no. of emetic episodes | Mean no. of retches |
|---|---|---|---|
| Cisplatin (9 mg/kg i.p.) | 99.2 (± 8.8) | 6 (± 2) | 43 (± 10) |
| Cisplatin (9 mg/kg i.p.) + test compound (1 mg/kg i.p.) | emetic response completely abolished | | |

The following example illustrates the preparation of a compound of formula (I). Temperatures are in °C. Where indicated, solutions were dried over $Na_2SO_4$ and solids were dried in vacuo over $P_2O_5$ at 50° overnight. Chromatography was carried out using the technique described by W. C. Still et al (J. Org. Chem., 1978, 43, 2923–2925), on kieselgel 9385.

EXAMPLE 1,2,3,9-Tetrahydro-9-methyl-3-[(2-methyl-1H-imidazol-1-yl) methyl]-4H-carbazol-4-one hydrochloride A solution of 2,3,4,9-tetrahydro-N,N,N,9-tetramethyl-4-oxo-1H-carbazole-3-methanaminium iodide (2.0 g) and 2-methylthiazole (5.0 g) in dry dimethylformamide (30 ml) was stirred, under nitrogen, at 95° for 16.75 h and then allowed to cool. The solid that crystallised was filtered off, washed with ice-cold, dry dimethylformamide (3×2 ml) and dry ether (2×10 ml) and then dried. The resulting solid (0.60 g) was suspended in a mixture of absolute ethanol (30 ml) and ethanolic hydrogen chloride (1 ml), and warmed gently to obtain a solution, which was filtered whilst warm. The filtrate was then diluted with dry ether to deposit a solid (0.6 g) which was recrystallized from absolute ethanol to give the title compound as a solid (0.27 g) m.p. 186–187°.

Analysis Found: C,61.9;H,6.4;N,11.8.

$C_{18}H_{19}N_3O.HCl.H_2O$ requires C,62.3;H,6.1;N,12.1%.

The following examples illustrate pharmaceutical formulations for use according to the invention, containing 1,2,3,9-tetrahydro-9-methyl-3-[(2-methyl-1H-imidazol-1-yl)methyl]-4H-carbazol-4-one hydrochloride dihydrate as the active ingredient (1.25 g of the hydrochloride dihydrate contains 1.00 g of the free base). Other compounds of formula (I) may be formulated in a similar manner.

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

| Direct Compression | | |
|---|---|---|
| Tablet | mg/tablet | |
| Active Ingredient | 4.688 | 28.125 |
| Calcium Hydrogen Phosphate BP* | 83.06 | 87.75 |
| Croscarmellose Sodium NF | 1.8 | 1.8 |
| Magnesium Stearate BP | 0.45 | 0.45 |
| Compression weight | 90.0 | 118.0 |

*of a grade suitable for direct compression.

The active ingredient was passed through a 60 mesh sieve, blended with the calcium hydrogen phosphate, croscarmellose sodium and magnesium stearate. The resultant mix was compressed into tablets using a Manesty F3 tablet machine fitted with 5.5 mm, flat bevelled edge punches.

| Sub-Lingual Tablet | mg/tablet |
|---|---|
| Active Ingredient | 2.5 |
| Compressible Sugar NF | 62.5 |
| Magnesium Stearate BP | 0.5 |
| Compression Weight | 65.0 |

The active ingredient is sieved through a suitable sieve, blended with the excipients and compressed using suitable punches. Tablets of other strengths may be prepared by altering either the ratio of active ingredient to excipients or the compression weight and using punches to suit.

| Wet Granulation | |
|---|---|
| Conventional Tablet | mg/tablet |
| Active Ingredient | 2.5 |
| Lactose BP | 151.5 |
| Starch BP | 30.0 |
| Pregelatinised Maize Starch BP | 15.0 |
| Magnesium Stearate BP | 1.5 |
| Compression Weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose of the compression weight and using punches to suit.

| Sub-Lingual Tablet | mg/tablet |
|---|---|
| Active Ingredient | 2.5 |
| Mannitol BP | 56.5 |
| Hydroxypropylmethylcellulose | 5.0 |
| Magnesium Stearate BP | 1.5 |
| Compression Weight | 65.5 |

The active ingredient is sieved through a suitable sieve and blended with the mannitol and hydroxypropylmethylcellulose. Suitable volumes of purified water are added and the powders are granulated. After drying, the granules are screened and blended into tablets using suitable punches.

Tablets of other strengths may be prepared by altering the ratio of active ingredient to mannitol or the compression weight and punches to suit.

| CAPSULES | mg/tablet |
|---|---|
| Active Ingredient | 2.5 |
| *Starch 1500 | 97.0 |
| Magnesium Stearate BP | 1.0 |
| Fill Weight | 100.0 |

*a form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

SYRUP

This may be either a sucrose or sucrose free presentation.

| A. Sucrose Syrup | mg/5 ml dose |
|---|---|
| Active Ingredient | 2.5 |
| Sucrose BP | 2750.0 |
| Glycerine BP | 500.0 |
| Buffer | |
| Flavour | |
| Colour | as required |
| Preservative | |
| Purified Water BP to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup is clarified by filtration.

| B. Sucrose-Free | mg/5 ml dose |
|---|---|
| Active Ingredient | 2.5 |
| Hydroxypropylmethylcellulose USP (viscosity type 4000) | 22.5 |
| Buffer | |
| Flavour | |
| Colour | as required |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

INJECTION

The injection may be administered by the intravenous or subcutaneous route.

| Injection | µg/ml |
|---|---|
| Active Ingredient | 50    800 |
| Dilute Hydrochloric Acid BP to | pH 3.5 to pH 3.5 |
| Sodium Chloride Injection BP to | 1 ml to 1 ml |

The active ingredient was dissolved in a suitable volume of Sodium Chloride Injection BP, the pH of the resultant solution was adjusted to pH 3.5 with dilute hydrochloric acid BP then the solution was made to volume with sodium chloride injection BP and thoroughly mixed. The solution was filled into Type 1 clear glass 5 ml ampoules which were sealed under a headspace of air, by fusion of the glass then sterilised by autoclaving at 120° for not less than 15 minutes.

| METERED DOSE PRESSURISED AEROSOL | | |
|---|---|---|
| Suspension Aerosol | mg/metered dose | Per can |
| Active Ingredient micronised | 0.250 | 66 mg |
| Oleic Acid BP | 0.020 | 5.28 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The Oleic Acid is mixed with the Trichlorofluoromethane at a temperature of 10°–15° C. and the micronised drug is mixed into the solution with a high shear mixer. The suspension is metered into aluminium aerosol cans and suitable metering valves, delivering 85 mg of suspension are crimped onto the cans and the Dichlorodifluoromethane is pressure filled into the cans through the valves.

| Solution Aerosol | mg/metered dose | Per can |
|---|---|---|
| Active Ingredient | 0.25 | 30.0 mg |
| Ethanol BP | 7.500 | 1.80 g |
| Trichlorofluoromethane BP | 18.875 | 4.35 g |
| Dichlorodifluoromethane BP | 48.525 | 11.65 g |
| Oleic Acid BP, on a suitable surfactant e.g. Span 85 (sorbitan trioleate) may also be included). | | |

The active ingredient is dissolved in the ethanol together with the Oleic Acid or surfactant if used. The alcoholic solution is metered into suitable aerosol containers followed by the trichlorofluoromethane. Suitable metering valves are crimped onto the containers and dichlorodifluoromethane is pressure filled into them through the valves.

| Inhalation Cartridges | mg/cartridge |
| --- | --- |
| Active Ingredient (micronised) | 0.5 |
| Lactose BP to | 25.00 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler.

We claim:

1. A method of treatment of nausea and vomiting which comprises administering to a human or animal subject in need thereof an effective amount for the treatment of nausea and vomiting of a compound of formula (Ia)

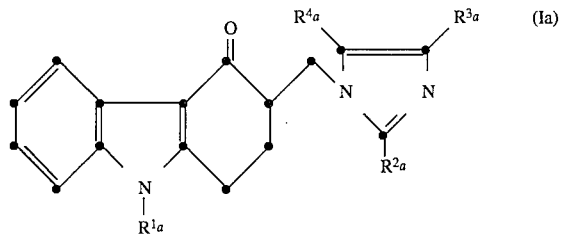

wherein $R^{1a}$ represents a hydrogen atom or a methyl, ethyl, propyl, prop-2-yl, prop-2-enyl or cyclopentyl group; $R^{3a}$ represents a hydrogen atom; and either $R^{2a}$ represents a methyl, ethyl, propyl or prop-2-yl group and $R^{4a}$ represents a hydrogen atom or $R^{2a}$ represents a hydrogen atom and $R^{4a}$ represents a methyl or ethyl group or a physiologically acceptable salt or solvate thereof.

2. A method of treatment of nausea and vomiting induced by an anti-cancer drug which is cisplatin, which comprises administering to a human or animal subject in need thereof an effective amount for the treatment of nausea and vomiting of a compound of formula (Ia)

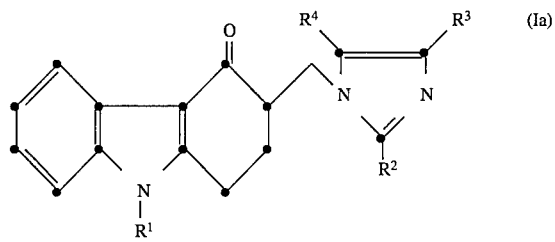

wherein $R^{1a}$ represents a hydrogen atom or a methyl, ethyl, propyl, prop-2-yl, prop-2-enyl or cyclopentyl group; $R^{3a}$ represents a hydrogen atom; and either $R^{2a}$ represents a methyl, ethyl, propyl or prop-2-yl group and $R^{4a}$ represents a hydrogen atom or $R^{2a}$ represents a hydrogen atom and $R^{4a}$ represents a methyl or ethyl group or a physiologically acceptable salt or solvate thereof.

* * * * *